United States Patent
Shen et al.

(10) Patent No.: US 7,164,015 B2
(45) Date of Patent: Jan. 16, 2007

(54) NON-CRYOGENIC PROCESS FOR FORMING GLYCOSIDES

(75) Inventors: Lifen Shen, North Brunswick, NJ (US); San Kiang, Madison, NJ (US); Zhenrong Guo, East Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/788,825

(22) Filed: Feb. 27, 2004

(65) Prior Publication Data

US 2004/0230045 A1  Nov. 18, 2004

Related U.S. Application Data

(60) Provisional application No. 60/451,210, filed on Feb. 27, 2003.

(51) Int. Cl.
*C07H 15/00* (2006.01)
*C07H 1/02* (2006.01)

(52) U.S. Cl. ...................... 536/124; 536/4.1
(58) Field of Classification Search ................ 536/4.1, 536/124
See application file for complete search history.

(56) References Cited

U.S. PATENT DOCUMENTS

| 5,534,328 A | 7/1996 | Ashmead et al. |
| 5,690,763 A | 11/1997 | Ashmead et al. |
| 6,069,238 A | 5/2000 | Hitchcock et al. |
| 2001/0029294 A1 | 10/2001 | Nickel et al. |

FOREIGN PATENT DOCUMENTS

EP  1 123 734  8/2001

OTHER PUBLICATIONS

Czernecki, S. et al. J. Org. Chem. 1991, 56, 6289-6292.*
Hawley's Condensed Chemical Dictionary, 13th Edition, 1997, p. 180.*
Hackh's Chemical Dictionary, 5th edition, 1987, p. 436.*
Barrett, A. G. M. et al., "Total Synthesis and Structural Elucidation of the Antifungal Agent Papulacandin D", J. Org. Chem., 1996, 61, pp. 1082-1100.
Barrett, A. G. M. et al., "Total Synthesis of the Antifungal Agent Papulacandin D", J. Chem. Soc., Chem. Commun., 1995, pp. 1147-1148.
Greene, T.W. et al., Protective Groups in Organic Synthesis, Third Edition, John Wiley & Sons, Inc., publ. (1999)(table of contents).
Manabe, S. et al., "Toward Synthesis of Novel C-glycoprotein from Human RNase; Unexpected Stereochemistry of Epoxide Opening Reaction by Organolithium Reagents in the Presence of Lewis Acid", Chemistry Letters, pp. 919-920 (1998).
Rosenblum, S.B. et al., "Synthesis of the Papulacandin C-Arylglucosyl Spiroketal Nucleus", J. Am. Chem. Soc., vol. 112, No. 7, pp. 2746-2748 (1990).
Sollogoub, M. et al., "First Synthesis of 1-deazacytidine, the C-nucleoside analogue of cytidine", Tetrahedron Letters, vol. 43, pp. 3121-3123 (2002).
Greene, T.W. et al., Protective Groups in Organic Synthesis, Third Edition, John Wiley & Sons, Inc., publ. (1999) (table of contents).
Manabe, S. et al., "Toward Synthesis of Novel C-glycoprotein from Human RNase; Unexpected Stereochemistry of Epoxide Opening Reaction by Organolithium Reagents in the Presence of Lewis Acid", Chemistry Letters, pp. 919-920 (1998).
Rosenblum, S.B. et al., "Synthesis of the Papulacandin C-Arylglucosyl Spiroketal Nucleus", J. Am. Chem. Soc., vol. 112, No. 7, pp. 2746-2748 (1990).

* cited by examiner

*Primary Examiner*—Shaojia Jiang
*Assistant Examiner*—Ganapathy Krishnan
(74) *Attorney, Agent, or Firm*—Burton Rodney (57) ABSTRACT

The present invention provides a method for making glycoside compounds including the steps of: (a) lithiating an aromatic reactant having a leaving group using a lithium reagent in a first microreactor under non-cryogenic conditions to form a lithiated anion species, and (b) coupling the lithiated anion species with a carbonyl substituted reactant to form a glycoside.

26 Claims, 3 Drawing Sheets

NON-CRYOGENIC PROCESS FOR FORMING GLYCOSIDES

This application claims a benefit of priority from U.S. Provisional Application No. 60/451,210 filed Feb. 27, 2003, the entire disclosure of which is herein incorporated by reference.

BACKGROUND OF THE INVENTION

1. Field of the Invention

The present invention relates generally to improved methods of making glycoside compounds using non-cryogenic techniques.

2. Description of the Background Art

Glycosides are compounds containing a carbohydrate and a non-carbohydrate residue in the same molecule. The carbohydrate residue, also referred to as the glycone, is attached by an acetyl linkage via a carbon atom to the non-carbohydrate residue of aglycone. Glycosides are compounds that are useful, inter alia, as intermediates in a variety of chemical processes and as pharmaceutically active compounds.

Glycosides are difficult to synthesize. In one widely used synthesis route, which involves reaction of a protected sugar with a metalated aromatic via nucleophilic addition, hydrogen abstraction to the lactone tends to occur. Only with careful attention to conditions for the addition of the sugar and metalated aromatic, and selection of appropriate hydroxyl protecting groups, have these synthesis routes produced an acceptable yield. Rosenblum, S. B. and Bihovsky, R., *J. Am. Chem. Soc.* 1990, 112, 2746–2748. One approach to address this problem, has been to perform batch processes under cryogenic conditions. However, in these synthesis routes, failure to use cryogenic conditions results in side reactions that produce unacceptable amounts of impurities.

In one conventional batch method, in a first reaction vessel under cryogenic conditions, a halogenated aromatic reactant is lithiated using an organo lithium reagent in the presence of a solvent to form a lithiated anion species. Under cryogenic conditions, the lithium anion species is transferred to a second reaction vessel. A reactant having a carbonyl functional group is coupled to the lithiated anion species in the presence of a solvent to form a protected form of the glycoside product. The protected form is then deprotected by reaction with methanesulfonic acid in methanol to form the desired glycoside end product. The cryogenic conditions are maintained by using a liquid nitrogen blanket. Liquid nitrogen is typically a temperature of about −196° C. The transfer line for the lithiated anionic species is maintained at about −78° C. or below. See, for example, Manabe, S. and Ito, Y.; Ogawa, T., *Chem. Lett.* 1998, 919–920; and Sollogoub, M., et al., *Tetrahedron Lett.* 2002, 43, 3121–3123.

The lithiating and the coupling steps are each highly exothermic reactions and proceed very quickly. For this reason the conventional lithiating and coupling steps must be performed under cryogenic conditions at about −80° C. and under a nitrogen blanket. The yield for this process is about 70%. The following Scheme A is representative of the conventional method:

Scheme A - Conventional Synthesis of Glycosides

The definitions of the symbols used and terms used in Scheme A are as follows:

TMS is trimethyl silane; THF is tetrahydrofuran; $R_1$ is hydrogen, $NO_2$, $OR_4$, a halogen, or a substituted or non-substituted alkyl, aryl, or heterocycle, wherein $R_4$ is a substituted or non-substituted alkyl or aryl; $R_2$ is a substituted or non-substituted alkyl group; $X_1$ is a heteroatom; and PG is a protective group.

In the conventional method shown in Scheme A, cryogenic conditions (i.e., temperatures of about −78° C.) are necessary because of the exothermic and rapid nature of the lithiating and coupling steps. Allowing these reactions to proceed at normal temperatures results in formation of excessive amounts of impurities. Specifically, the lithiated anion species is unstable and has a tendency to undergo nucleophilic substitution with BuBr, a side product of reaction. To avoid formation of this impurity, transfer of the lithiated anion species to a reaction vessel must be performed, also under cryogenic conditions. Thus, it is necessary to pre-cool the lithiated anion species and cold trace the transfer line to the second reaction vessel. Coupling of the lithiated anion species to the carbonyl reactant must also be performed under cryogenic conditions. As a result, the conventional batch process requires two cryogenic reactors, one for synthesis of the lithiated starting material, and one for the coupling reaction.

Failure to maintain these stringent cryogenic conditions results in low yields and the presence of impurities. Even with temperatures as low as −10° C., a calculated yield is only about 30%. The reaction profile for reactions at these temperatures using the conventional method suggests that there is less than 50% of the desired product in the reaction mixture.

Drawbacks of the conventional methods of making the glycosides of interest include those typically associated with cryogenic processes in general. Namely, it is necessary to bring starting materials to cryogenic conditions before reacting. The lithiated anion intermediate must also be cryogenically stored and cold traced in the transfer to the coupling reaction vessel. The coupling reaction vessel must also be maintained under cryogenic conditions. This involves elevated costs related to specially designed reaction vessels and transfer lines capable of withstanding the very low temperatures involved.

Cryogenic reactions are also of concern from a safety perspective, as using liquid nitrogen as a coolant can cause burns upon contact with skin and also poses a risk of explosion if not used in conjunction with pressure relief equipment. Additionally, the addition of reagent must be closely regulated to avoid an increase in temperature which risks low yield and formation of undesirable side products, as discussed infra. Slow addition of reagent results can increase reaction time necessary to obtain end product.

Accordingly, there is a present need for a method of making glycosides that does not require costly cryogenic reaction vessels, transfer lines, or pre-cooling of starting materials, that reduces risk of formation of undesirable side products, and that provides an acceptable yield of product.

Known techniques for optimizing wet chemistry processes include close regulation of temperature, pressure, mixing conditions, relative volumes of reactants, catalysts, and the like. In order to achieve or better regulate these optimization parameters, microreactors have been developed. A microreactor is a miniaturized reaction system containing one or more reaction channels having sub-millimeter dimensions. Examples of microreactors include those disclosed in U.S. patent application Ser. No. 20010029294, U.S. Pat. Nos. 5,534,328, 5,690,763, and E.P.O. Patent No. EP 1123734.

Microreactors vary in structure but generally include a series of stacked plates having openings for fluid transfer. The microreactors will have an input port for introduction of reactants and an output port for discharge of a chemical product. In addition, heat transfer fluid pathways are also incorporated into the design to perform a heat exchange function. Using microreactors allows transfer of heat and mass much more quickly than in standard wet chemistry methods, resulting in improved control of rates of reaction and addition of reactants. Specifically, using microreactors allows more accurate control over the reaction temperature of exothermic or endothermic reactions. Additionally, reactants can be heated or cooled immediately upon entry into the reactor. Although microreactors have been used to provide more accurate control of temperature per se, they have not traditionally been used to perform those reactions which must be performed under cryogenic conditions. Furthermore, to date, methods of making glycosides using microreactor technology have not been developed.

It would be a useful advantage to have methods of making glycoside compounds that include a process which consumes reactive reagents as they are made and that does not require cryogenic conditions to be performed.

SUMMARY OF THE INVENTION

The present invention is generally directed to a method of making glycoside compounds though a non-cryogenic or a combination of non-cryogenic and cryogenic batch or continuous process. The novel methods of the invention reduce formation of undesirable by products, provide improved yields, and reduce costs of manufacture.

The present invention provides a method of preparing glycosides using a non-cryogenic process, including the steps of: (a) lithiating an aromatic reactant having a leaving group using a lithium reagent in a first microreactor under non-cryogenic conditions to form a lithiated anion species; and (b) coupling the lithiated anion species with a carbonyl substituted reactant to form a glycoside.

Also provided is a method of making a glycoside having the general structural formula [I]:

wherein: $R_1$ is hydrogen, $NO_2$, $OR_4$, a halogen, or a substituted or non-substituted alkyl, aryl, or heterocycle; $R_2$ is a substituted or non-substituted alkyl group, wherein $R_4$ is a substituted or non-substituted alkyl or aryl; $X_1$ is a heteroatom; and PG is a protective group, the method including the steps of: (a) reacting an aromatic reactant having general structural formula [II]:

wherein: $R_1$ is as defined previously and $X_2$ is a leaving group, in a first microreactor with an organo lithium reagent to form a lithiated anion species having general structural formula [III]:

wherein R$_1$ is as defined previously, and (b) coupling the lithiated anion species [III] with a carbonyl substituted compound having general structural formula [IV]:

wherein: R$_2$, X$_1$ and PG are as described previously, to form the compound having general structural formula [I].

DETAILED DESCRIPTION OF THE INVENTION

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. SO$_2$ NH$_2$), substituted sulfonamido, nitro, cyano, carboxy, carbamyl (e.g. CONH$_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl. Where noted above where the substituent is further substituted it will be with halogen, alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl; substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy. The substituent may be further substituted by halo, hydroxy, alkyl, alkoxy, aryl, substituted aryl, substituted alkyl or aralkyl.

The term "cycloalkyl" refers to an optionally substituted, saturated cyclic hydrocarbon ring system, preferably containing 1 to 3 rings and 3 to 7 carbons per ring which may be further fused with an unsaturated C$_3$–C$_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle," "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofliryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl.

Exemplary substituents include one or more alkyl groups as described above or one or more groups described above as alkyl substituents. Also included are smaller heterocycles, such as, epoxides and aziridines.

The term "heteroatoms" shall include oxygen, sulfur and nitrogen.

The numbers in the subscript after the symbol "C" define the number of carbon atoms a particular group can contain. For example, "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$alkenediyl which bridges two groups; examples include ethylene-1,2-diyl (vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms; examples include ethynyl, propynyl, butynyl, and hexynyl.

"Heteroaryl" means a five- or six-membered aromatic ring containing at least one and up to four non-carbon atoms selected from oxygen, sulfur, and nitrogen. Examples of heteroaryl include thienyl, furyl, pyrrolyl, imidazolyl, pyrazolyl, thiazolyl, thiadiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings.

As used herein, the term cryogenic process means a process performed at a temperature of about −20° C. or below. Characteristically, cryogenic processes are performed at temperatures of about −60° C. or below.

As used herein, the term non-cryogenic process means a process performed at a temperature of greater than about −20° C.

The present invention is directed to methods for making certain glycoside compounds in an efficient and cost effective manner. The glycoside compounds of the present invention are useful end products or intermediates in a variety of chemical processes. In particular, the glycoside compounds may be converted to unprotected glycosides, including certain pharmaceutically active heterocyclic compounds. It has now been found that glycosides in general, and in particular the compounds represented by the general structural formula [I], may be produced at low cost in relatively high yields and with improved purity.

A microreactor useful for the method of the present invention may be constructed from a plurality of laminae that are stacked and bonded together. The surfaces of the laminae bear micromechanically created structures which interact to form reaction spaces for the chemical reactions. The microreactor should include at least two continuous channels connected to separate inlets and outlets that are pathways for chemicals and heat transfer fluid, respectively. A first channel is a reaction pathway including at least one inlet port for the receipt of reactants and at least one outlet port for the discharge of product. Desirably, the reaction pathway is from about 50 to about 600 microns in cross section.

A second channel is a heat transfer pathway, which is structurally integrated into the microprocessor. The heat transfer pathway conveys heat transfer liquid and acts as a heat exchanger. Presence of the heat transfer pathway allows for fast and precise heating and cooling of reactants. As a result, an independent temperature control mechanism is not required. Use of the microreactor allows for reactants to be kept at room temperature.

A suitable microreactor for use in the method of the invention is disclosed, for example, in E.P. Patent No. EP1123734, the entirety of which is herein incorporated by reference. The microreactor includes a plurality of plates in stacked arrangement so as to form a plurality of layers. Each plate has at least one opening which overlaps an opening of adjacent plates to form a pathway between at least some of the layers. Temperature control is achieved by using a combination of temperature sensors and heat exchangers. Each outer plate is fitted with either one or more inlet openings or one or more outlet openings.

Desirably, in the methods according to the invention, formation of the lithiated anion species proceeds in a continuous process. In this case, the risk of forming impurities is reduced, since there is no need for storing the lithiated anion species. Specifically, risk of nucleophilic substitution of the lithium anion with BuBr, a side-product of reaction, is reduced because as the lithiated anion species is formed, it proceeds directly to coupling with the carbonyl substituted reagent, rather than remaining in solution with BuBr.

Figure 1:
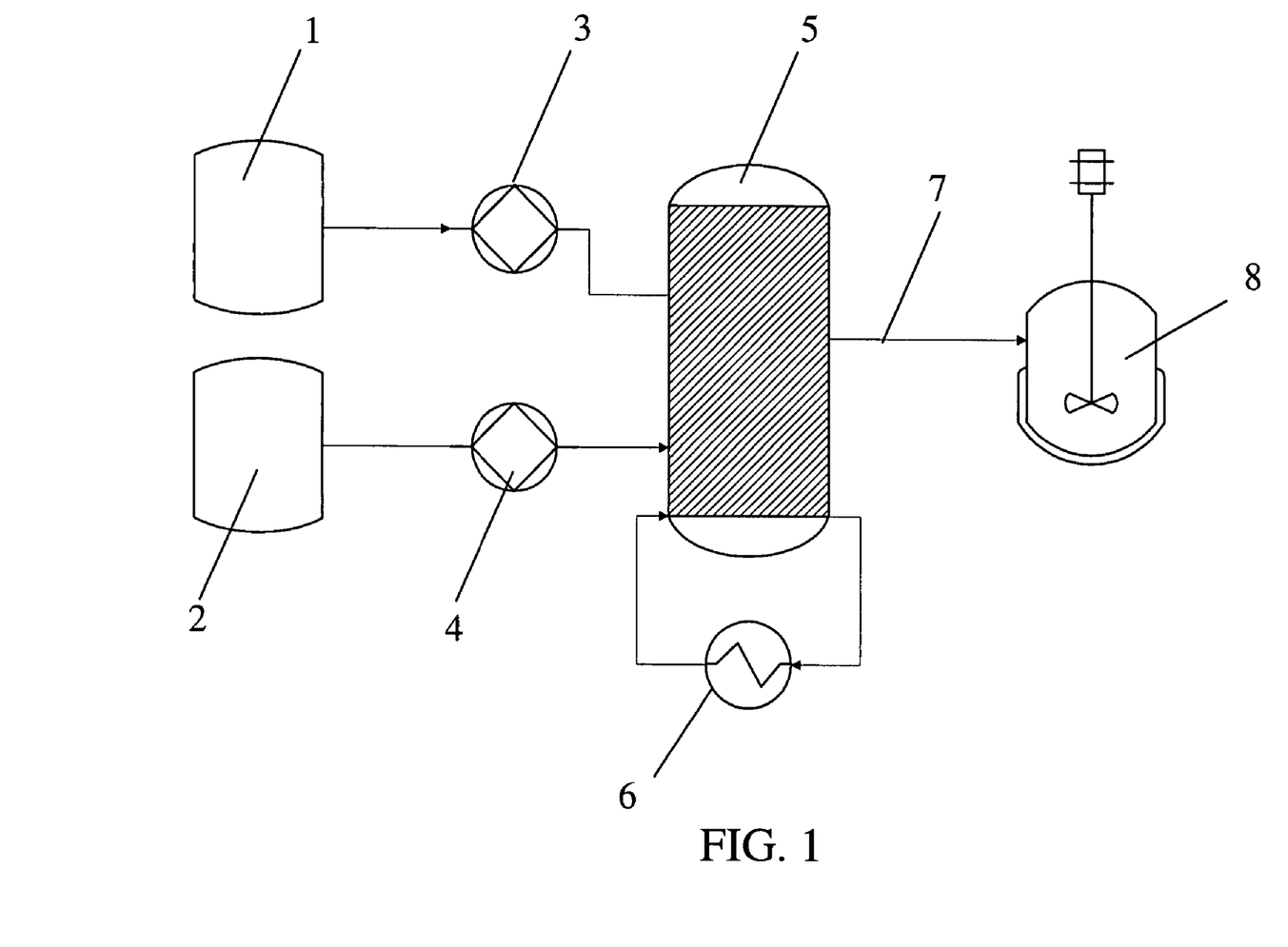
FIG. 1 is a schematic representation of an embodiment of the invention in which a part of the synthesis is performed in a conventional reaction vessel and a part of the synthesis is performed in a microreactor.

Referring now to FIG. 1, a process flow diagram of a first embodiment of the present invention is shown. In this embodiment, an aromatic reactant having a leaving group is stored in a first vessel 1 at room temperature. A lithium reagent is stored in a second vessel 2, also at room temperature. The aromatic reactant and the lithium reagent are transferred at a predetermined rate from the vessels 1 and 2 via pumps 3 and 4, respectively to a microreactor 5. The temperature of a reaction to produce a lithiated anion species is regulated in the microreactor 5 by a chiller 6. The lithiated anion species is fed through a cold traced transfer line 7 from the microreactor 5 to a conventional cryogenic reactor 8. The conventional cryogenic reactor 9 includes a carbonyl substituted reactant and is maintained at a temperature of −78° C. during the course of the reaction. The end product of this reaction may be the desired end product. If so, the synthesis is complete. Alternatively, the glycoside formed in the conventional cryogenic reactor 8 may be further processed, using conventional methods.

Figure 2:
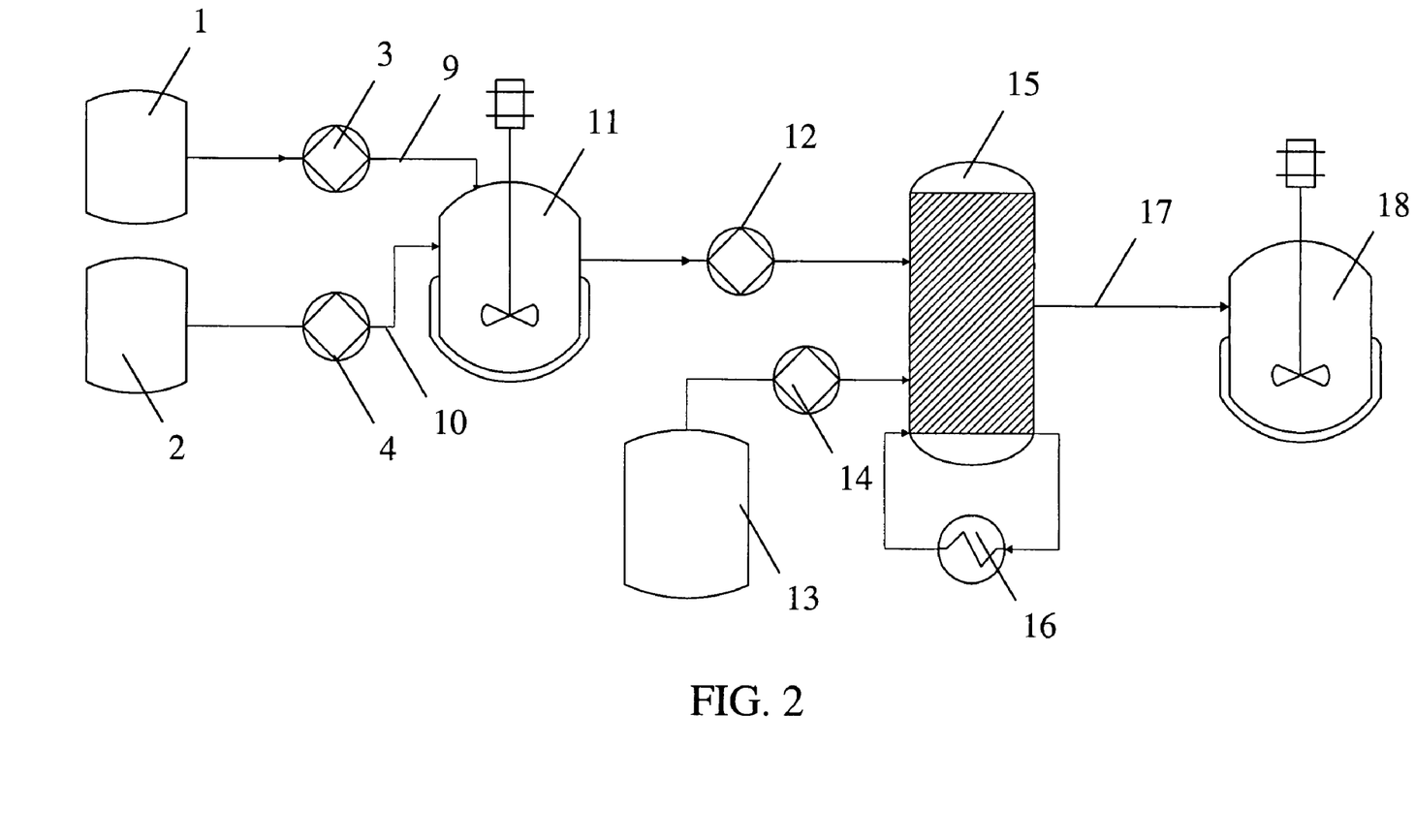
FIG. 2 is a schematic representation of an alternative embodiment of the invention in which a part of the synthesis is performed in a microreactor and a part of the synthesis is performed in a conventional reaction vessel.

Referring now to FIG. 2, a process flow diagram of a second embodiment of the present invention is shown. In this embodiment, as in the previous embodiment, an aromatic reactant having a leaving group is stored in a first vessel 1 at room temperature. A lithium reagent is stored in a second vessel 2, also at room temperature. The contents are transferred to a conventional cryogenic reactor 11 via cold traced lines, 9 and 10, respectively. Flow from the first vessel 1 and the second vessel 2 is regulated by pumps 3 and 4, respectively. The reaction produces a lithium anion species.

The lithium anion species derived from this reaction is then fed into a microreactor 15. Flow is regulated by a pump 12. A carbonyl substituted reagent stored in a third vessel 13, which may be at room temperature, is transferred to the microreactor 15 at a predetermined flow rate via pump 14. The temperature of a reaction in the microreactor 15 is regulated by a chiller 16 to produce a glycoside. This glycoside may be the desired end product. Alternatively, the glycoside from the microreactor 15 may be fed into a conventional reactor 18 along a conventional transfer line 17, where it may be further reacted to produce other useful glycosides or other end products using conventional process steps.

Figure 3:
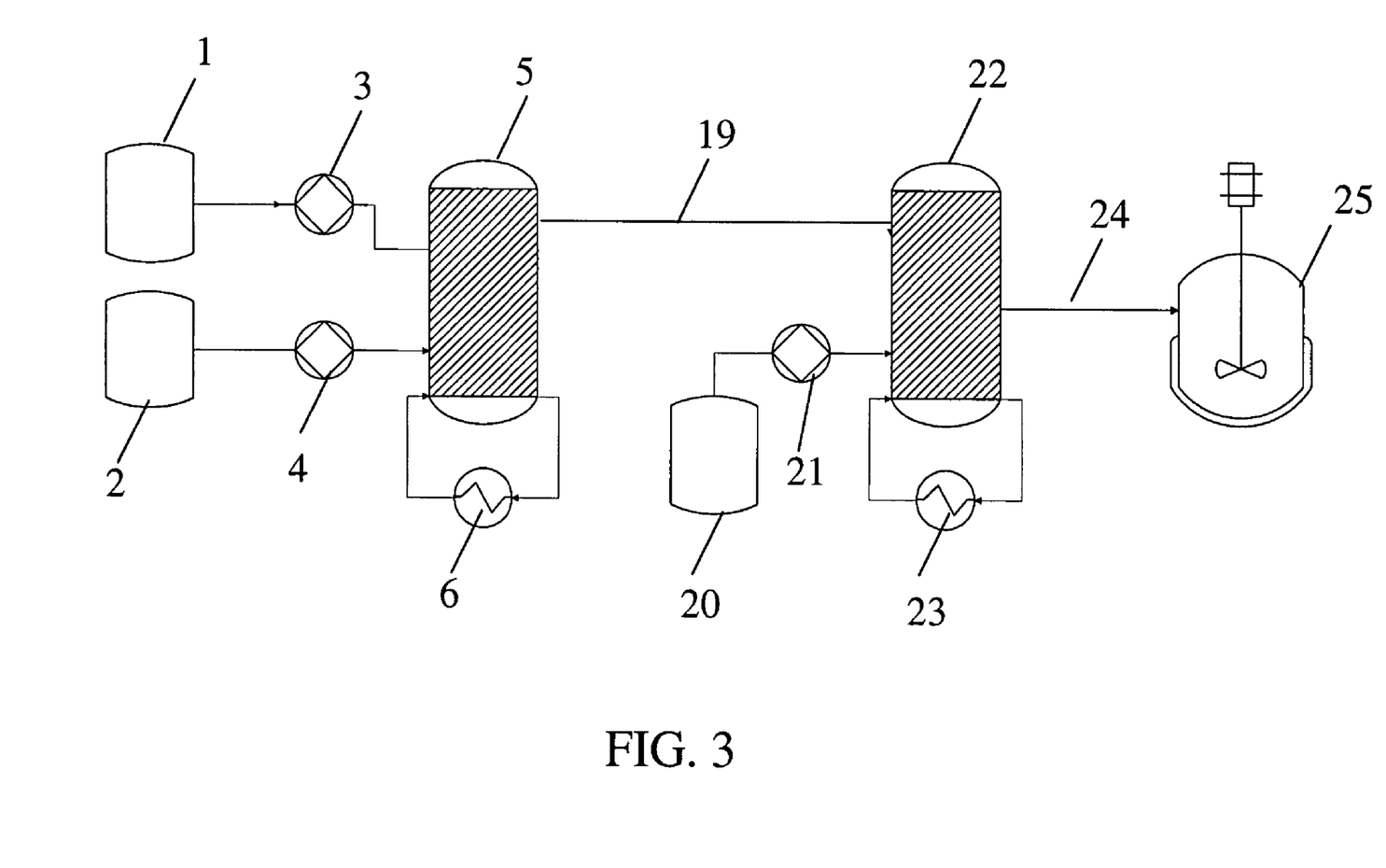
FIG. 3 is a schematic representation of an alternative embodiment of the invention in which the entire synthesis is performed in a plurality of microreactors.

Referring now to FIG. 3, a schematic process flow diagram of a third embodiment of the present invention is shown. In this embodiment, the entire process is performed under non-cryogenic conditions. An aromatic reactant having a leaving group is stored in a first vessel 1 at room temperature. A lithium reagent is stored in a second vessel 2, also at room temperature. The aromatic reactant and the lithium reagent are transferred at a predetermined rate from the vessels 1 and 2 via pumps 3 and 4, respectively to a first microreactor 5. The temperature of a reaction to produce a lithiated anion species is regulated in the first microreactor 5 by a chiller 6.

The lithiated anion species thus formed is fed directly from the first microreactor 5 to a second microreactor 22 along a conventional transfer line 19. A carbonyl substituted reactant stored in a third vessel 20 at room temperature is transferred at a predetermined flow rate via pump 21 to the second microreactor 22. A reaction to produce a glycoside end product is regulated in the second microreactor 22 by a second chiller 23.

The glycoside thus formed may be further processed. In this case, the protected glycoside formed in the second microreactor 22 is fed into a conventional reactor 25 via a conventional transfer line 24. The conventional reactor 25 may contain, for example, reagents such as $MeSO_3/MeOH$, which are useful in deprotecting the hydroxyl groups and converting a 1-hydroxyl glycoside to a 1-methoxyl glycoside. Alternatively, the protected glycoside may be collected in the conventional reactor 25 and subsequent reactions, such as the deprotecting reaction, may be performed by addition of suitable reagent thereto. Further additional reactions may also be performed in the conventional reactor 25. Useful reactions may include, for example, treating a 1-methoxyl glycoside with a trialkylsilane to removing the 1-methoxy group. The reactor 25 may be maintained at room or other non-cryogenic temperature during the course of any subsequent reactions.

Methods of Synthesizing Glycosides

An embodiment of the present invention as shown in FIG. 1, is illustrated below in Scheme B. In this embodiment, certain glycosides having general structural formula [I] are synthesized using a combination of non-cryogenic and cryogenic conditions.

The definitions of the symbols and terms used in Scheme B are as follows: $R_1$ is hydrogen, $NO_2$, $OR_4$, a halogen, or a substituted or non-substituted alkyl, aryl, or heterocycle, wherein $R_4$ is a substituted or non-substituted alkyl or aryl group; $R_2$ is a substituted or non-substituted alkyl group; $X_1$ is a heteroatom; $X_2$ is a leaving group such as a halogen; and PG is a synthetic organic "protecting group" of the type generally used to "protect" a hydroxyl functionality e.g. an acyl type group such as an acetyl, a trifluoroacetyl, an arylalkyl group like a benzyl or the like.

Referring now to Scheme B, it is to be understood that, depending on the end product desired, the reaction may proceed from step 1 to step 2, or may include further processing steps. It will be further understood that where typical or preferred conditions (i.e., reaction temperature, times, mole ratios of reactants, solvents, pressures, etc.) are given, other process conditions may also be used unless otherwise stated. Optimum reaction conditions may vary with the particular reactants, solvents or microreactors used, and such conditions may be determined by one skilled in the art through known routine optimization procedures. In the preparation of glycoside according to the formula (I), it has been observed that certain solvent combinations may be used to improve the yield of product (I). Such combinations include THF/toluene and THF/heptane, which generate yields of greater than about 80%.

In step 1, an R-substituted compound of general structural formula [II] reacts with a lithium reagent. Selection of the R-substituted compound [II] allows the introduction of an R-group on the compound of general formula [I].

The lithium reagent used is desirably an organo lithium reagent. Suitable organo lithium reagents include n-BuLi and t-BuLi. Others will be apparent to those having ordinary skill in the art.

The reaction is performed in a microreactor under non-cryogenic conditions. Desirably, the reaction temperature is from about −20° C. to about 20° C. More desirably, the reaction temperature is from about −10° C. to about 5° C. Most desirably, the reaction is performed at about −10° C. Rate of feed of compound [II] is determined by the particular microprocessor used. Generally, a flow rate which allows a residence time of about 2–3 seconds is sufficient. Depending on the particular microprocessor used, this represents a flow rate of reagents through the microreactor at a rate of from about 10 ml/min to about 200 ml/min. The resulting product is a lithiated anion species of general structural formula [III].

The reaction is performed in the presence of a suitable inert solvent or solvent mixture. Typical solvents known to those skilled in the art may be used in the reaction. Suitable solvent mixtures include, for example, tetrahydrofuran (THF)/toluene, THF/tert-butyl methyl ether (TBME), and THF/heptane. The THF/toluene is convenient as this solvent mixture is used in a later step of the process. Any solvent or mixture in which the reactants and the end product are soluble, and which provides acceptable product yield and quality, may be used. If the compounds can be dissolved in a single polar solvent, such solvent would also be desirable.

In step 2, the lithium anion species of formula [III] is fed directly into a conventional reactor used in cryogenic processes via a suitably vented cold traced transfer line. The conventional reactor contains an R-substituted compound according to general structural formula [IV] having a carbonyl functional group. Selection of the R-substituted compound [IV] allows the introduction of another R-group on the compound of general formula [I]. The R-substituted compound of formula [IV] is provided with protective groups. Suitable protecting or blocking groups used in organic synthesis are well known to the practitioner and are adequately described in the appropriate literature. See, e.g, Theodora Greene, *Protective Groups in Organic Synthesis*, John Wiley and Sons, New York. Desirably, the protective group is a per(silyl) group. Preferably, the protective group is selected from $Me_3Si$, $Et_3Si$, $Me_2SiBu$-t, and $C_6H_5CH_2$.

Reaction of the lithium anion of formula [III] with the compound of formula [IV] having a carbonyl functional group proceeds under cryogenic conditions in the presence of a suitable inert solvent mixture to form a glycoside according to general structural formula [I]. The amount of lithium anion added to the compound of formula [IV] in the reaction vessel is usually in the range of from 1–3 molar equivalents, preferably about 1.1 molar equivalents. The resulting product is a protected form of a glycoside intermediate having general structural formula [I].

The reaction in step 2 is performed in the presence of a suitable inert solvent or solvent mixture. Solvent mixtures mentioned above in step 1 are also suitable for this reaction. Typical solvents known to those skilled in the art may be used in the reaction. Suitable solvent mixtures include, for example, THF/toluene, THF/tert-butyl methyl ether, and THF/heptane.

The reaction is performed under cryogenic conditions. The lithium anion of formula [III] and the compound of formula [IV] must be pre-cooled prior to introduction into the cryogenic reactor. The temperature of the lithium anion upon introduction into the cryogenic reactor should be at least about −80° C. Desirably, the reaction temperature is maintained at a substantially constant temperature of about −78° C.

Step 2 of the process shown in Scheme B can also be performed under non-cryogenic conditions, as discussed infra in Scheme D.

An embodiment of the present invention as shown in FIG. 2, is illustrated below in Scheme C. In this embodiment, certain glycosides having general structural formula [I] are synthesized using a combination of cryogenic and non-cryogenic conditions.

Scheme C - Combination Cryogenic and Non-Cryogenic Microreactor Synthesis of Glycosides The definitions of the symbols and terms used in Scheme C are as defined previously.

The reaction shown in Scheme C will now be described. It is understood, that, depending on the end product desired, the reaction may proceed from step 1 to step 2, or may continue using conventional process steps. It will be further understood that where typical or preferred conditions (i.e., reaction temperature, times, mole ratios of reactants, solvents, pressures, etc.) are given, other process conditions may also be used unless otherwise stated. Optimum reaction conditions may vary with the particular reactants, solvents or microreactors used, and such conditions may be determined by one skilled in the art through known routine optimization procedures.

In step 1, an R-substituted compound of general structural formula [II] reacts with a lithium reagent under cryogenic conditions. As described previously, selection of the R-substituted compound [II] allows the introduction of an R-group on the compound of general formula [I]. The reactants are brought to cryogenic temperatures prior to introduction into a conventional cryogenic reactor. The reaction is performed in the presence of a suitable inert solvent or solvent mixture as defined previously. The lithium reagent is also as defined previously. The resulting product is a lithiated anion species of general structural formula [III].

The reaction temperature may be performed at a temperature of less than or equal to about −80° C. Preferably, the reaction temperature is performed at about −78° C.

In step 2, the lithium anion species of formula [III] is fed into a microreactor. An R-substituted compound according to general structural formula [IV] having a carbonyl functional group, which may be at room temperature, is also added to the microreactor. Selection of the R-substituted compound [IV] allows the introduction of another R-group on the glycoside compound having general formula [I].

compound of formula [IV] are not required to be pre-cooled prior to introduction into the microreactor. Desirably, the rate of production of the lithium anion will be comparable to the rate of introduction into the microreactor. Minimizing residence time in the cryogenic reactor of step 1 will facilitate good yield of the final product. The reaction temperature should be maintained at a temperature of from about −20° C. to about 20° C. Preferably, the reaction is performed at a temperature of about −10° C.

In each of the aforementioned synthesis schemes, the rate of introduction of reactants into the microreactor will vary depending on the particular microreactor used. Generally, a flow rate which allows a residence time of about 2–3 seconds is sufficient. The resulting product is a protected form of a glycoside having general structural formula [I].

A further embodiment of the invention as shown in FIG. 3 is illustrated below as Scheme D. In this embodiment, glycosides can be synthesized in a completely non-cryogenic process. In this scheme, the glycoside derived in step 2 may be the desired end product. Optionally, the glycoside may be further reacted using conventional process steps, as illustrated in step 3, to form other useful glycosides.

Reaction of the lithium anion of formula [III], with the compound of formula [IV], proceeds under non-cryogenic conditions in the presence of a suitable inert solvent mixture, as defined previously, to form a glycoside according to general structural formula [I].

The reaction of step 2 is performed under non-cryogenic conditions. The lithium anion of formula [III] and the The definitions of the symbols and terms used in Scheme D are as defined previously. Additionally, $R_3$ is an alkyl or benzyl group and $R_5$ is a lower alkyl group.

Referring now to Scheme D, it will be understood that where typical or preferred conditions (i.e., reaction temperature, times, mole ratios of reactants, solvents, pressures, etc.) are given, other process conditions may also be used unless otherwise stated. Optimum reaction conditions may vary with the particular reactants, solvents or microreactors used, and such conditions may be determined by one skilled in the art through known routine optimization procedures.

Step 1 is performed essentially as described above for Scheme B. Namely, step 1 is performed under non-cryogenic conditions, in the presence of a suitable inert solvent or solvent mixture. However, in contrast to Scheme B, transfer of the compound of formula [III] to a subsequent reactor is not required to be performed using cold traced transfer lines. Conventional transfer is possible when the lithium anion species thus formed is fed directly from a first microreactor to a second microreactor.

In step 2, which provides an additional non-cryogenic step, the lithium anion of formula [III] is fed from the first microreactor into a second microreactor which contains or is fed the compound of formula [IV] having a carbonyl functional group. Reaction of the lithium anion of formula [III] with the compound of formula [IV] proceeds under non-cryogenic conditions in the presence of a suitable inert solvent mixture to form a glycoside according to general structural formula [I]. Rate of feed of reactant(s) into the second microreactor is determined by the particular microprocessor used. Generally, a flow rate of from about 10 ml/min to about 200 ml/min, preferably from about 60 to about 150 ml/min is used. A residence time of about 2–3 seconds is usually sufficient. Preferably, the lithium anion species formed in Step 1 is generated at a rate comparable to the rate of feed into the second microreactor. Yields from this reaction are at least about 70%.

The reaction temperature may be from about −20° C. to about 20° C. Desirably, the reaction temperature is maintained at a substantially constant temperature of about −10° C.

Step 3 is an optional step which involves further reaction of the glycosides derived in step 2 to remove the protecting groups. The deprotection of the compound of the general formula [I] is preferably carried out under conditions which permit selective deprotection such as under acidic conditions or by well known common hydrogenation reaction or the like as known to one of ordinary skill in the art. The protective groups are removed by addition of a stoichiometric amount of a suitable organic acid or mixture containing an acid, for example, $MeSO_3H/MeOH$, TsOH, and $CF_3COOH$. The molar ratios are not critical. The reaction may be performed in a conventional reactor at room temperature or it can be performed at the same temperature used in the preceding step. Exemplary proportions of the organic acid to the compound of formula [I] may range from 1–3:1 molar equivalents. These proportions are now limiting to the invention. The rate of addition of the organic acid to the compound of formula [I] in the conventional reactor is desirably between about 5 ml/min and 15 ml/min. The resulting product is a deprotected glycoside having general structural formula [V]:

[V]

wherein $R_1$, $R_2$, $R_3$ and $X_1$ are as defined previously.

Thus, removal of the protecting groups yields the deprotected compound [V]. After completion of the reaction, the desired product can be isolated and purified according to techniques widely known in the field of organic chemistry (e.g. precipitation, solvent extraction, recrystallization, and chromatography). The deprotected compound may itself be a useful intermediate or end product. It should be noted, however, that a deprotecting step may not be necessary in certain chemical reactions. Rather, use of this step is dependent on the intended use of the reaction product. The compound may be further reacted to obtain pharmaceutically acceptable acid addition or base salts thereof using methods that will be known to those having ordinary skill in the art.

The compounds of formula [VIII] can exist in the form of salts. Such salts include addition salts with inorganic acids such as, for example, hydrochloric acid and sulfuric acid, and with organic acids such as, for example, acetic acid, citric acid, methanesulfonic acid, toluene sulfonic acid, tartaric acid, and maleic acid. Further, in case the compounds of the general formula [VIII] of this invention contain an acidic group, the acidic group can exist in the form of alkali metal salts such as, for example, a potassium salt and a sodium salt; alkaline earth metal salts such as, for example, a magnesium salt and a calcium salt; and salts with organic bases such as ethylammonium salt and an arginine salt.

EXAMPLE 1

Synthesis of a Glycoside Compound of Formula [I]

A synthesis procedure for making a glycoside compound of the general formula [I] was performed according to Synthesis Scheme E.

Scheme E - Combination Cryogenic and Non-Cryogenic Process for Preferred Glycosides

[IIa]

n-BuLi, −10° C.
THF/toluene
Non-cryogenic microreactor

-continued

[Scheme showing reaction of compound IVa (TMSOCH₂-substituted pyranone with TMSO groups) plus compound IIIa (lithiated biphenyl with Et group) under Cryogenic THF/toluene, -78° C., MeSO₃H/MeOH, yielding compound Va (HOCH₂-substituted pyranose with OMe and OH groups, bearing biphenyl-Et substituent).]

[IVa]   [IIIa]   [Va]

The definitions of the symbols and terms used in Scheme E are as follows:

THF is tetrahydrofuran; Bu is butyl; TMS is a trimethylsily moiety; Me is a methyl moiety; and Et is an ethyl moiety.

A solution of an aromatic reactant [IIa] in THF/toluene solvent was lithiated with n-BuLi in a microreactor (CYTOS Lab System, available from Cellular Process Chemistry Systems, Frankfurt, Germany). The microreactor was maintained at a temperature of −10° C. using a chiller (available from Thermo Haake, Karlsruhe, BW, Germany). The flow rate of the lithium reagent into the microreactor was maintained in the range of from about 10 to about 50 ml/min. The flow rate of the aromatic reagent into the microreactor was maintained in the range of from about 10 to about 50 ml/min. A residence time in the microreactor was 2–3 seconds.

From the microreactor, lithiated anion [IIIa] was transferred as generated in a continuous flow to a conventional cryogenic reactor (available from Chemglass Vineland, N.J.) containing a carbonyl reagent [IVa] in toluene via a cold traced transfer line. The reactor was cryogenically maintained at −78° C. during the course of the reaction. The reaction proceeded to completion in 0.5 hours. The reaction was quenched with MeSO₃H/MeOH to produce the desired glycoside [Va]. Yield was 80–85%.

The quality of the glycoside so derived was analyzed by HPLC, LC-MS, $^1$H and $^{13}$C NMR. All spectroscopic data were consistent with the structure. The yield of glycoside was calculated from the standard curve derived by HPLC analysis. Yield was calculated to be about 80–85%.

It will be understood that where typical or preferred conditions (i.e., reaction temperature, times, mole ratios of reactants, solvents, pressures, etc.) are given, other process conditions may also be used unless otherwise stated. Optimum reaction conditions may vary with the particular reactants or solvent used, and such conditions may be determined by one skilled in the art through known routine optimization procedures.

What is claimed is:

1. A method of making glycosides using a non-cryogenic process comprising, in a continuous process, the steps of:
   (a) lithiating an aromatic reactant having a leaving group using a lithium reagent in a first microreactor at non-cryogenic temperatures to form a lithiated anion species; and
   (b) coupling the lithiated anion species with a carbonyl substituted reactant at non-cryogenic temperatures to form a glycoside.

2. The method according to claim 1, wherein said lithiating step is performed at a temperature of from about −10° C. to about 20° C.

3. The method according to claim 2, wherein said lithiating step is performed at a temperature of from about −10° C. to about 5° C.

4. The method according to claim 1, wherein the residence time in said first microreactor is from about 2 seconds to about 3 seconds.

5. The method according to claim 1, wherein said aromatic reactant is a halide.

6. The method according to claim 1, where said lithium reagent is selected from the group consisting of n-BuLi and t-BuLi.

7. The method according to claim 1, wherein said coupling step is performed in a second microreactor under non-cryogenic conditions.

8. The method according to claim 7, wherein said coupling step is performed at a temperature of from about −20° C. to about 20° C.

9. The method according to claim 8, wherein said coupling step is performed at a temperature of about −10° C.

10. The method according to claim 7, wherein the residence time in said second microreactor is from about 2 seconds to about 3 seconds.

11. The method according to claim 7, wherein a yield of said glycoside is greater than about 70%.

12. A method of making glycosides using a non-cryogenic process comprising, in a continuous process, the steps of:
   (a) lithiating an aromatic reactant having a leaving group wing a lithium reagent at non-cryogenic temperatures to form a lithiated anion species; and
   (b) coupling the lithiated anion species with a carbonyl substituted reactant according to formula IV

[Structure IV: pyranone ring with PGOR₂-CH₂ substituent, X₁ heteroatom, C=O, and three OPG substituents]

[IV]

wherein
   X₁ is a heteroatom;
   R₂ is a substituted or unsubstituted alkyl group; and
   PG is a protective group, in a microreactor under non-cryogenic temperatures to form a glycoside.

13. The method according to claim 12, wherein said coupling step is performed at a temperature of from about −10° C. to about 200° C.

14. The method according to claim 12, wherein said coupling step is performed at a temperature of from about −10° C. to about 5° C.

15. The method according to claim 12, wherein the residence time in said microreactor is from about 2 seconds to about 3 seconds.

16. The method according to claim 12, further comprising the step of:
   (c) deprotecting the glycoside.

17. A continuous process for making a glycoside having the general structural formula [I]:

wherein: $R_1$ is hydrogen, $NO_2$, $OR_4$, a halogen, or a substituted or non-substituted alkyl, aryl, or heterocycle; $R_2$ is a substituted or non-substituted alkyl group; $R_4$ is a substituted or non-substituted alkyl or aryl; $X_1$ is a heteroatom; and PG is a protective group, the method including the steps of:

(a) reacting an aromatic reactant having general structural formula [II]:

wherein: $R_1$ is as defined previously and $X_2$ is a leaving group, in a first microreactor with an organo lithium reagent at non-cryogenic temperatures to form a lithiated anion species having general structural formula [III]:

wherein $R_1$ is as defined previously, and (b) coupling the lithiated anion species [III] with a carbonyl substituted compound having general structural formula [IV]:

wherein: $R_2$, $X_1$ and PG are as described previously, at non-cryogenic temperatures to form the compound having general structural formula [I].

18. The method of claim 17 wherein the lithiating step is performed at a temperature of from about −10° C. to 20° C.

19. The method of claim 18 wherein the coupling step is performed in a second microreactor at non-cryogenic temperatures.

20. The method of claim 18 wherein the lithiating step is conducted in a solvent selected from THF/toluene or THF/heptane.

21. The method of claim 18 wherein the coupling step is performed in a second microreactor at non-cryogenic temperatures.

22. The method of claim 21 wherein the coupling step is performed at a temperature of from about −20° C. to 20° C.

23. The method of claim 12 wherein PG is a per(silyl) group.

24. The method of claim 23 wherein PG is $Me_3Si$, $Et_3Si$ or $Me_2SiBu$-t.

25. The method of claim 17 wherein PG is a per(silyl) group.

26. The method of claim 25 wherein PG is $Me_3Si$, $Et_3Si$ or $Me_2SiBu$-t.

\* \* \* \* \*

UNITED STATES PATENT AND TRADEMARK OFFICE
CERTIFICATE OF CORRECTION

PATENT NO. : 7,164,015 B2  Page 1 of 1
APPLICATION NO. : 10/788825
DATED : January 16, 2007
INVENTOR(S) : Lifen Shen et al.

It is certified that error appears in the above-identified patent and that said Letters Patent is hereby corrected as shown below:

On the Title Page, Item [56] References Cited, the following appears twice, but should only appear once, therefore, please delete the following:

"Greene, T.W. et al., Protective Groups in Organic Synthesis, Third Edition, John Wiley & Sons, Inc. publ. (1999) (table of contents).

Manabe, S. et al., "Toward Synthesis of Novel C-glycoprotein from Human RNase; Unexpected Stereochemistry of Epoxide Opening Reaction by Organolithium Reagents in the Presence of Lewis Acid", Chemistry Letters, pp. 919-920 (1998).

Rosenblum, S.B. et al., "Synthesis of the Papulacandin C-Arylglucosyl Spiroketal Nucleus", J. Am. Chem. Soc., vol. 112, No. 7, pp. 2746-2748 (1990)."

In Column 3, line 25, please delete "bums" and insert -- burns --.

In Column 4, line 25, please delete "though" and insert -- through --.

In Column 17, line 17, please delete "trimethylsily" and insert -- trimethylsilyl --.

In Column 18, Claim 12, line 38, please delete "wing" and insert -- using --.

In Column 18, Claim 13, line 58, please delete "200° C" and insert -- 20° C --.

In Column 19, Claim 17, line 17, please delete "alkyl ," and insert -- alkyl, --.

Signed and Sealed this

Twenty-fourth Day of February, 2009

JOHN DOLL
*Acting Director of the United States Patent and Trademark Office*